(12) United States Patent
Kong (10) Patent No.: US 11,027,116 B2
(45) Date of Patent: Jun. 8, 2021

(54) SYSTEM AND METHOD FOR EAR-ARRANGED TRANSCUTANEOUS VAGUS NERVE STIMULATION

(71) Applicant: The General Hospital Corporation, Boston, MA (US)

(72) Inventor: Jian Kong, Malden, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/778,344

(22) PCT Filed: Nov. 23, 2016

(86) PCT No.: PCT/US2016/063552
§ 371 (c)(1),
(2) Date: May 23, 2018

(87) PCT Pub. No.: WO2017/091705
PCT Pub. Date: Jun. 1, 2017

(65) Prior Publication Data
US 2018/0339148 A1 Nov. 29, 2018

Related U.S. Application Data (60) Provisional application No. 62/258,684, filed on Nov. 23, 2015.

(51) Int. Cl.
*A61N 1/04* (2006.01)
*A61N 1/36* (2006.01)
(Continued)

(52) U.S. Cl.
CPC ........... *A61N 1/0456* (2013.01); *A61M 21/00* (2013.01); *A61N 1/0472* (2013.01);
(Continued)

(58) Field of Classification Search
CPC .................... A61N 1/0456; A61N 1/36036
See application file for complete search history.

(56) References Cited

U.S. PATENT DOCUMENTS

| | | | | |
|---|---|---|---|---|
| 6,074,422 A | * | 6/2000 | Berrang | A61N 1/0541 607/137 |
| 6,077,237 A | * | 6/2000 | Campbell | G06F 3/011 600/587 |

(Continued)

FOREIGN PATENT DOCUMENTS

| | | |
|---|---|---|
| CN | 2118545 U | 10/1992 |
| CN | 101564334 A | 10/2009 |

(Continued)

OTHER PUBLICATIONS

Barbanti, et al., Non-Invasive Vagus Nerve Stimulation for Acute Treatment of High-Frequency and Chronic Migraine: An Open-Label Study, Journal of Headache and Pain, 2015, 16:61, 5 pages.

(Continued)

*Primary Examiner* — John R Downey
(74) *Attorney, Agent, or Firm* — Quarles & Brady LLP (57) ABSTRACT

A transcutaneous nerve stimulation system includes a multifunctional earphone assembly that receives a sound signal from a sound source or other sources (such as a signal generator). An amplifier receiving the sound signal from the sound source or independent signal generator amplifies the sound signal to generate an amplified electrical signal. A stimulator, which includes multiple conductive electrode contacts, is coupled to the amplifier to receive the amplified electrical signal. The electrode contacts may protrude from an earbud/headphone or extend from an adjustable probe arm. The amplified electrical signal is used to apply electrical stimulation while the earphone assembly emits audible sounds according to the sound signal. The combined functionality enhances compliance with treatment regimens (Continued)

involving electrical stimulation of vagus nerves and other regions of a subject. Potential indications include, without limitation, major depressive disorder, epilepsy, chronic pain, pre-diabetes, insomnia, cardiovascular disorders, tinnitus, autism, daily stress, and anxiety.

17 Claims, 8 Drawing Sheets

(51) Int. Cl.
    *A61N 1/37*     (2006.01)
    *A61M 21/00*     (2006.01)

(52) U.S. Cl.
    CPC .......... *A61N 1/36025* (2013.01); *A61N 1/37* (2013.01); *A61M 2021/0027* (2013.01); *A61M 2021/0055* (2013.01); *A61M 2205/502* (2013.01); *A61N 1/36036* (2017.08)

(56) References Cited

U.S. PATENT DOCUMENTS

| | | | | |
|---|---|---|---|---|
| 6,354,299 | B1* | 3/2002 | Fischell | A61N 1/36025 128/899 |
| 7,769,461 | B2 | 8/2010 | Whitehurst | |
| 9,415,220 | B1* | 8/2016 | Spinelli | G06F 19/34 |
| 10,130,809 | B2* | 11/2018 | Cartledge | A61N 1/05 |
| 2008/0021517 | A1* | 1/2008 | Dietrich | A61N 1/36017 607/57 |
| 2008/0051852 | A1* | 2/2008 | Dietrich | A61H 39/002 607/45 |
| 2008/0103407 | A1* | 5/2008 | Bolea | A61N 1/0556 600/529 |
| 2013/0282070 | A1* | 10/2013 | Cowan | A61N 1/37217 607/3 |
| 2014/0078462 | A1* | 3/2014 | Abreu | G02C 3/003 351/111 |
| 2014/0126752 | A1* | 5/2014 | Beck | A61N 1/36014 381/151 |
| 2014/0330334 | A1* | 11/2014 | Errico | A61N 1/36025 607/45 |
| 2014/0330336 | A1* | 11/2014 | Errico | A61N 1/36021 607/45 |
| 2015/0012059 | A1* | 1/2015 | Kim | A61N 1/36032 607/57 |
| 2015/0360030 | A1* | 12/2015 | Cartledge | A61N 1/36036 607/60 |
| 2016/0142832 | A1* | 5/2016 | Hillbratt | H03F 1/34 381/317 |

FOREIGN PATENT DOCUMENTS

| | | |
|---|---|---|
| CN | 103908747 A | 7/2014 |
| CN | 105056394 A | 11/2015 |

OTHER PUBLICATIONS

Basic, et al., The Effect of Vagus Nerve Stimulation on Migraine in Patient with Intractable Epilepsy: Case Report, Neurological Sciences, 2013, 34(5):797-798.

Cecchini, et al., Vagus Nerve Stimulation in Drug-Resistant Daily Chronic Migraine With Depression: Preliminary Data, Neurological Sciences, 2009, 30(Suppl 1):S101-S104.

Daban, et al., Safety and Efficacy of Vagus Nerve Stimulation in Treatment-Resistant Depression. A Systematic Review, Journal of Affective Disorders, 2008, 110(1-2):1-15.

Fang, et al., Transcutaneous Vagus Nerve Stimulation Modulates Default Mode Network in Major Depressive Disorder, Biological Psychiatry, 2016, 79:266-273.

George, et al., Potential Mechanisms of Action of Vagus Nerve Stimulation for Depression, in Vagus Nerve Stimulation, Second Edition, edited by Schachter, et al., 2003, pp. 68-83.

Goadsby, et al., Effect of Noninvasive Vagus Nerve Stimulation on Acute Migraine: An Open-Label Pilot Study, Cephalalgia, 2014, 34(12):986-993.

Hein, et al., Auricular Transcutaneous Electrical Nerve Stimulation in Depressed Patients: A Randomized Controlled Pilot Study, J Neural Transm, 2013, 120:821-827.

Henry, Therapeutic Mechanisms of Vagus Nerve Stimulation, Neurology, 2002, 59(Suppl 4):S3-S14.

Huang, et al., Effect of Transcutaneous Auricular Vagus Nerve Stimulation on Impaired Glucose Tolerance: A Pilot Randomized Study, BMC Complementary and Alternative Medicine, 2014, 14:203, 8 pages.

Lenaerts, et al., Can Vagus Nerve Stimulation Help Migraine?, Cephalalgia, 2008, 28:392-395.

Nemeroff, et al., VNS Therapy in Treatment-Resistant Depression: Clinical Evidence and Putative Neurobiological Mechanisms, Neuropsychopharmacology, 2006, 31:1345-1355.

Peuker, et al., The Nerve Supply of the Human Auricle, Clinical Anatomy, 2002, 15:35-37.

Rong, et al., Transcutaneous Vagus Nerve Stimulation for the Treatment of Depression: A Study Protocol for a Double Blinded Randomized Clinical Trial, BMC Complementary and Alternative Medicine, 2012, 12:255, 6 pages.

Rong, et al., Transcutaneous Vagus Nerve Stimulation for Refractory Epilepsy: A Randomized Controlled Trial, Clinical Science, 2014, CS May 18, 2013 [Abstract Only].

Rong, et al., Effect of Transcutaneous Auricular Vagus Nerve Stimulation on Major Depressive Disorder: A Nonrandomized Controlled Pilot Study, J Affect Disord., 2016, 195:172-179.

Sackeim, et al., Physical Treatments in Psychiatry, in Treatment of Depression: Bridging the 21st Century, M.M. Neissman, Editor, 2001, American Psychiatric Press, pp. 151-174.

Silberstein, et al., Chronic Migraine Headache Prevention with Noninvasive Vagus Nerve Stimulation, The EVENT Study, Neurology, 2016, 87:529-538.

Stefan, et al., Transcutaneous Vagus Nerve Stimulation (t-VNS) in Pharmacoresistant Epilepsies: A Proof of Concept Trial, Epilepsia, 2012, 53(7):e115-e118.

Trevizol, et al., Transcutaneous Vagus Nerve Stimulation (taVNS) for Major Depressive Disorder: An Open Label Proof-of-Concept Trial, Brain Stimulation, 2016, 9:453-454.

Ventureyra, Transcutaneous Vagus Nerve Stimulation for Partial Onset Seizure Therapy, Child's Nerv Syst, 2000, 16:101-102.

PCT International Search Report and Written Opinion, PCT/US2016/063552, dated Feb. 6, 2017.

China National Intellectual Property Administration, Notice on the First Office Action for application 201680079770.7. dated Apr. 14, 2020. With Translation.

* cited by examiner

SYSTEM AND METHOD FOR EAR-ARRANGED TRANSCUTANEOUS VAGUS NERVE STIMULATION

CROSS-REFERENCE TO RELATED APPLICATIONS

This application is a U.S. National Phase of PCT Application No. PCT/US2016/063552 filed on Nov. 23, 2016 which is related to, and incorporates herein by reference in its entirety, U.S. Application Ser. No. 62/258,684, filed Nov. 23, 2015, and entitled "Combined Earplug and Transcutaneous Vagus Nerve Stimulation."

FIELD OF THE INVENTION

This document concerns an invention relating generally to delivery of sound and auricular peripheral neuromodulation using a multifunctional earphone (headphone/earbud) assembly.

BACKGROUND

The vagus nerve is the longest cranial nerve, traveling from the medulla in the brain to the colon. The vagus nerve innervates thoracic and abdominal organs, supplying motor parasympathetic fibers to all organs except the adrenal glands. The vagus nerve is involved in the autonomic, cardiovascular, respiratory, gastrointestinal, immune, and endocrine systems, and it helps regulate heart rate, blood pressure, vascular resistance, airway diameter, respiration, and feeding. The vagal afferent nerves (i.e., the nerves carrying nerve impulses from sensory receptors or sense organs towards the central nervous system) sense such stimuli as pressure, pain, stretch, temperature, osmotic pressure, and inflammation; regulatory information is conveyed through vagal efferent nerves (i.e., the nerves that carry nerve impulses away from the central nervous system towards the peripheral effector organs). Because of the extensive reach of the vagus nerve, stimulating the vagus nerve has been used or investigated for the treatment of a great variety of disorders.

In recent years, peripheral neural modulation, particularly auricular transcutaneous vagus nerve stimulation (stVNS), has been gaining popularity. Vagus nerve stimulation (VNS) is an FDA-approved somatic treatment for such disorders as treatment-resistant depression (TRD), for which it can produce significant and clinically meaningful antidepressant effects. However, the need for surgery, perioperative risks, and potentially significant side effects have limited the use of this treatment. To overcome the potential barriers of applying VNS, a non-invasive VNS method, i.e., transcutaneous vagus nerve stimulation (tVNS), has been developed. The rationale for using tVNS on the ear is based on anatomical studies that suggest the ear is the only place on the surface of the human body where there is afferent vagus nerve distribution. Thus, direct stimulation of the afferent nerve fibers on the ear should produce an effect similar to classic VNS in reducing (for example) depressive symptoms, but without the burden of surgical intervention.

Treatment of symptoms via electrical stimulation, including via tVNS, may require stimulation for many hours each week, or even multiple hours each day. For example, treating symptoms of TRD may require two or more hours of treatment each day, and this may be an unrealistic commitment for many patients. Consequently, despite its great potential, the benefits of tVNS may not be realizable for many patients due to a lack of compliance with the necessary treatment regimens. What is needed is an effective system, device, and method for vagal nerve stimulation capable of achieving desired results with enhanced levels of compliance.

In another patent application (US 2015/0360030) is described an attempt to use a modified earbud to stimulate the ear canal, along with a clip for use in stimulating other parts of the ear. However, stimulating the ear canal can have side effects, such as damage to hearing, and vagus physiological responses such as dizziness and discomfort in the throat. In addition, the privacy/confidentiality of users may not be fully protected. Also, users must obtain an integrated device, which is limited in its ability to provide different stimulation patterns/frequencies/waveforms. The device is also limited in its ability to ensure the highest quality sound.

Thus, there is a need for transcutaneous nerve stimulation devices and methods that: 1) can be conveniently secured to existing personal earbuds, without diminishing sound quality or requiring users to deviate from personal device preferences; 2) can be used with existing stimulators, such as transcutaneous electrical nerve stimulation (TENS) devices, so that a user is not required to have another stimulator, and may have more options of stimulation frequency, waveforms, and patterns; 3) includes flexible, adherable, and/or exchangeable electrodes that can be more comfortable and that can accommodate different ear sizes, such as the smaller ears of children; 4) provide headphone versions that do not require contact with the ear canal; 5) offer the option for users who just use the headphone to isolate outside noises while maintaining the flexibility of being able to adjust the location and size of the electrodes to apply stimulation; and/or 6) can protect privacy, if desired, by being difficult to perceive from observations of the earphone.

SUMMARY

The present disclosure provides exemplary systems, devices, and methods for transcutaneous vagus nerve stimulation ("tVNS") using a multifunctional earphone assembly. "Earphone" here is used to refer generally to devices that can be secured to the head or ear, and that can emit sounds. As used herein, earphones can have many different configurations, including (for example) earbuds that are inserted in the ear canal, and/or headphones worn over the head or otherwise with various portions that are worn over, on, or around a user's head or ear in various ways, and may partly or wholly cover one or both ears of the subject. The earphone assembly includes a listening unit that receives a sound signal from a sound source, such as a smartphone, tablet, radio, or media player. The listening unit includes an electroacoustic transducer (i.e., a speaker), and is able to emit ("play") the audio that is output, in the form of the sound signal, by the sound source. An amplifier receiving the sound signal from the sound source amplifies the sound signal to generate an amplified electrical signal. A stimulator coupled to the amplifier is used to apply electrical stimulation using the amplified electrical signal while the listening unit emits audible sounds according to sound signal. The amplified electrical signal from the amplifier is used to transcutaneously stimulate an area with vagus nerve distribution (or other region) of a subject. The (substantially unamplified) sound signal thus provides the audible sounds produced by the listening unit while the amplified electrical signal simultaneously provides electrical stimulation. The listening unit may receive the sound signal via the amplifier, or it may receive the sound signal directly from the sound source that provides the sound signal that is amplified by the amplifier. Alternatively, the unit can also be used with various existing headphones/earbuds and/or electrical stimulators (such as TENS devices) that may be available separately.

Exemplary tVNS systems can be implemented in various configurations. For example, a sound source, a control module (or a separate market-available stimulator device, such as a TENS device) with controller and amplifier, and an earphone assembly (which can be an earbud available from other makers) can be separate components. A user may connect the sound source to one or more "inputs" of the control module, and connect the earphone assembly to an "output" of the control module. In alternative versions, one or both of the controller and the amplifier (or TENS device) could be incorporated into the earphone assembly. In such a configuration, the user would connect the earphone assembly to a separate sound source. In other alternative versions, the sound source, controller, amplifier, and earphone assembly could be incorporated into one unit/device. The user would have one device that includes various media, and that is capable of emitting sound and simultaneously applying electrical stimulation to stimulate a vagus nerve or other part of a subject's body.

The listening unit and stimulator of the earphone assembly can also be implemented in various configurations. For example, the stimulator may include one or more stimulating electrode contacts directly secured to an earbud of the listening unit, and may include a conductive resin or elastomer (such as conductive rubber). One or more electrode contacts of the stimulator may be secured to a probe arm that extends upwardly from the listening unit. The probe arm may be rotatable and/or pivotable to accommodate different applications and users. In other implementations, the earphone assembly may include a probe unit that can be adjustably separated from the listening unit to different degrees. A shaft may connect the earphone and probe units, and the two may be pulled apart and brought back together as the shaft is pulled out or inserted into one or both of the earphone and probe units via sliding or "screw" action. The electrodes can be exchangeable based on the size of the user's ear. The assembly can also be provided with exchangeable silicone "sticky" electrodes to enhance comfort of the stimulation. Also, the set of electrodes can be independently attached to existing earbuds, allowing users to use preferred earbuds they already possess. In addition, stimulators separately available for purchase can be used as electrical stimulators, allowing for more electrical stimulation patterns, frequencies, and waveform options that have been (or will be) demonstrated to be effective for various disorders in clinical studies. Finally, a headphone configuration can partly or wholly conceal the electrodes, which will enhance the privacy of users.

Because the superficial vagus nerve branches out in the ear, a earphone assembly that combines an earphone with tVNS is advantageous. The combined function of playing media and applying electrical stimulation capitalizes on the area of the ear with vagus nerve distribution. The sound (music, audiobook, audio track of a video, etc.) signal is amplified to stimulate the vagus nerve while an individual is, for example, listening to music or watching a video. Providing stimulation while users are engaged in media of their choosing will make treatments more convenient, and the greater ease will enhance compliance. Potential indications for the system include, but are not limited to, major depressive disorder, epilepsy, chronic pain, pre-diabetes, insomnia, cardiovascular disorders, tinnitus, and autism. The system may also serve as a preventative measure against daily stress and anxiety, for example.

The foregoing and other aspects and advantages of the invention will appear from the following description. In the description, reference is made to the accompanying drawings which form a part hereof, and in which there is shown by way of illustration one or more preferred embodiments of the invention. Such embodiments do not necessarily represent the full scope of the invention, however, and reference is made therefore to the claims for interpreting the scope of the invention.

DETAILED DESCRIPTION

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures. The figures depict selected embodiments and are not intended to limit the scope of embodiments of the invention. Skilled artisans will recognize the examples provided herein have many useful alternatives that fall within the scope of embodiments of the invention.

The invention may be described herein in terms of functional and/or logical block components and various processing steps. It should be appreciated that such block components may be realized by any number of hardware, software, and/or firmware components configured to perform the specified functions. For example, an embodiment may employ various integrated circuit components, e.g., memory elements, digital signal processing elements, logic elements, diodes, look-up tables, etc., which may carry out a variety of functions under the control of one or more microprocessors or other control devices. Other embodiments may employ program code, or code in combination with other circuit components. It should also be appreciated that certain components and functions may be shared and/or shuffled between blocks and among blocks in different embodiments of the invention, as deemed suitable. For example, the role of a processing unit may range from giving a command to initiate a self-directed protocol, without coordination by the processing unit, or it may take a more active role in the steps involved in implementing a particular protocol.

Figure 1A:
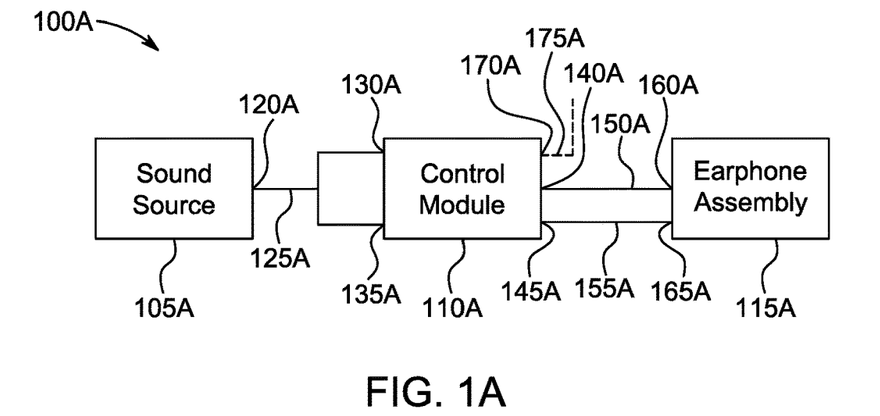
FIGS. 1A-1C show three exemplary arrangements for a sound source, a control module, and an earphone assembly.
Figure 1B:
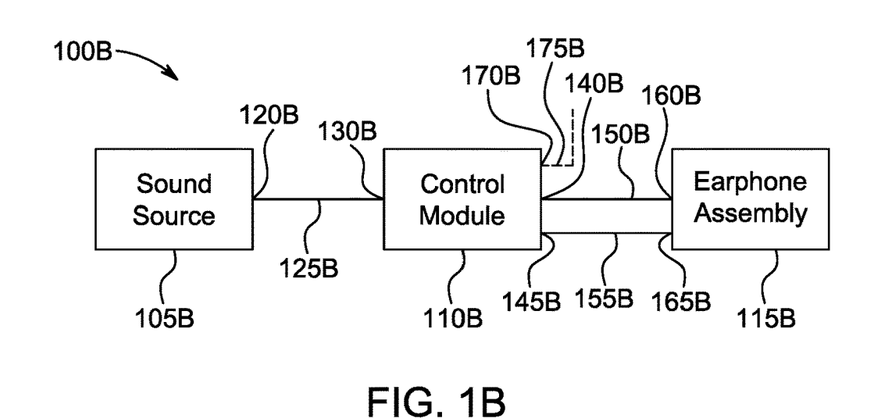
Figure 1C:
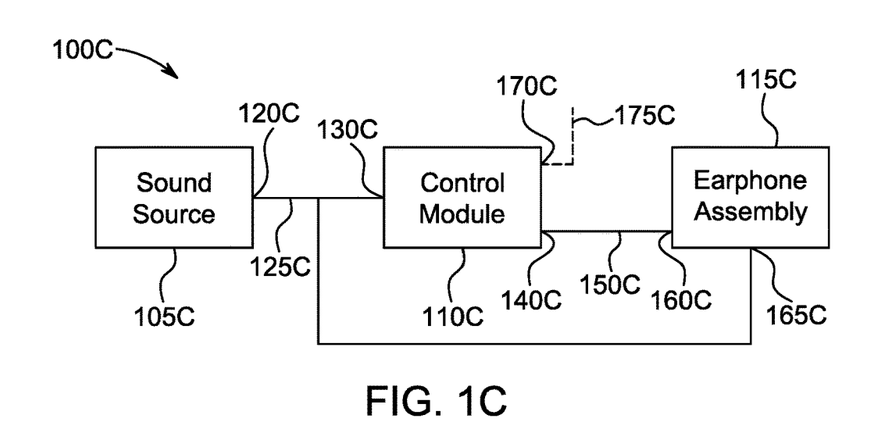

Referring initially to FIGS. 1A, 1B, and 1C, each of the exemplary arrangements 100A-C includes a sound source 105A-C, a control module 110A-C, and an earphone assembly 115A-C. Each sound source 105A-C includes a sound source output port 120A-C for outputting a sound signal 125A-C, respectively. In arrangement 100A, the sound signal 125A is split (using a splitter), and received in first and second control module input ports 130A, 135A. In arrangement 100B, the sound signal 125B is received in a single control module input port 130B, and the control module 110B splits the sound signal 125B internally. In arrangement 100C, the sound signal 125C is split and received in a control module input port 130C and an earphone sound input port 165C.

Once the sound signal 125A-C has been received by the control module 110A-C, the control module 110A-C generates an amplified electrical signal 150A-C that is output via a control module electrical signal output port 140A-C. In arrangement 100A, the control module 110A also outputs the unamplified sound signal 155A through a control module sound signal output port 145A. In arrangement 100B, the control module 110B splits the sound signal 125B and outputs an unamplified sound signal 155B through a control module sound signal output port 145B.

The earphone assembly 115A-C includes an earphone electrical signal input port 160A-C for receiving the amplified electrical signal 150A-C from the control module 110A-C. The earphone assembly 115A-C also includes an earphone sound signal input port 165A-C, but in arrangements 100A and 100B, the sound signals received in the earphone sound signal input ports 165A and 165B are the unamplified sound signals 155A and 155B from the control modules 110A and 110B, respectively. In arrangement 100C, the sound signal received in the earphone sound signal input port 165C of the earphone assembly 115C is the split up sound signal 125C from the sound source 105C.

As an optional feature, the control module 110A-C can include one or more auxiliary amplified electrical signal output ports 170A-C for outputting auxiliary amplified electrical signals 175A-C. Such additional outputs from the control module 110A-C allow for the application of supplemental stimulation of other parts of the body, as deemed suitable for various treatments. Such a configuration is well-suited for treating disorders that may respond to simultaneous stimulation at multiple parts of the body.

Figure 2A:
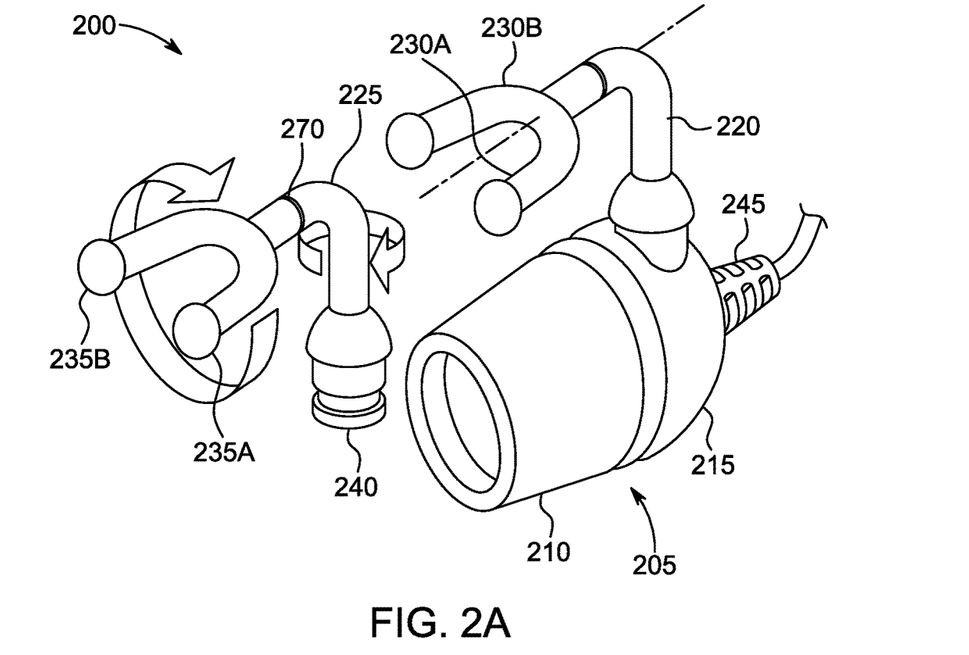
FIG. 2A shows an exemplary earphone assembly with a listening unit and a probe arm with a pair of conductive stimulating electrode contacts or exchangeable silicone sticky electrodes with different sizes for enhancing contact between the electrodes and the skin to enhance comfort levels during stimulation (so as to avoid, for example, a "needling" (needle-like) sensation on the skin).
Figure 2B:
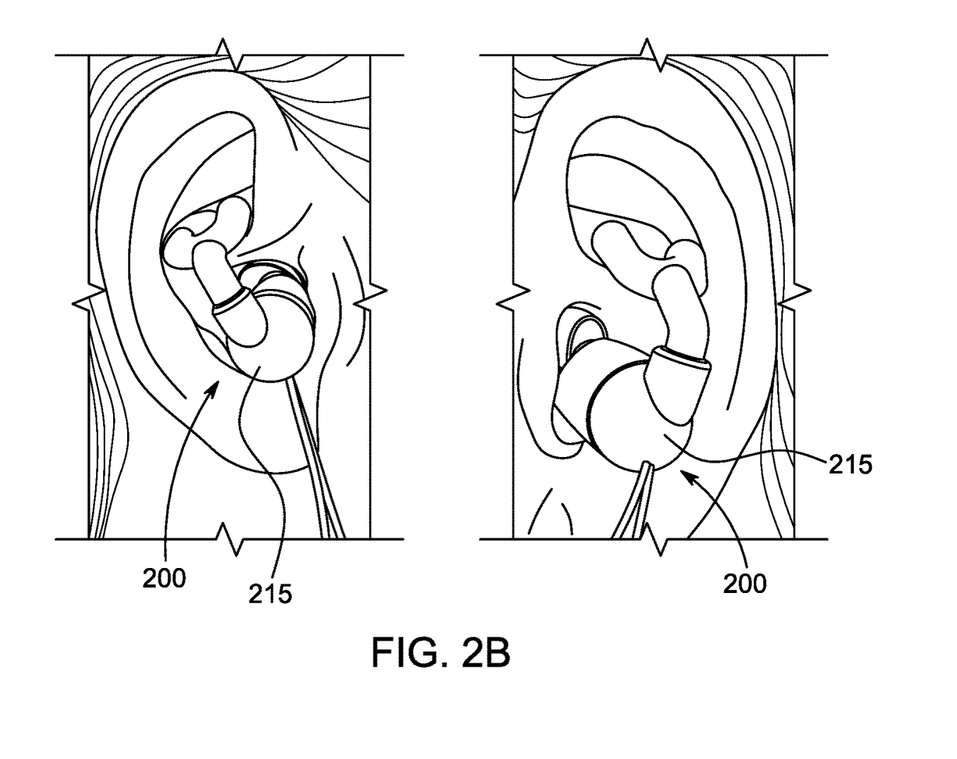
FIG. 2B shows the exemplary earphone assembly of FIG. 2A in use in the ears of a subject.

Turning to FIGS. 2A and 2B, exemplary earphone assembly 200 includes a listening unit 205 having a flexible (soft) earbud 210 extending from a rigid (hard) rear support 215. Extending upwardly from the rear support 215 is a probe arm 220 (which may be adjustably bent at a probe elbow 225) branching into a pair of prongs 230A, 230B. The prongs 230A, 230B terminate in electrode contacts 235A, 235B, respectively. The electrode contacts 235A, 235B, which are conductive, are part of a stimulator of the earphone assembly for use in applying electrical stimulation. They may include electrodes similar to the ones used in transcutaneous electrical nerve stimulation ("TENS") applications, conductive resins, and conductive elastomers. The probe arm 220 is secured to the rear support 215 via a rotating fixture 240, which allows the probe arm 220 to rotate about its long axis relative to the listening unit 205. The branched prongs 235A, 235B of the probe arm 220 are also rotatable at joint 270. The listening unit 205 includes a speaker for emitting audible sounds from the earbud 210 and into the ear canal, as shown in FIG. 2B. The sound signal and amplified electrical signal (as well as power from a power supply) are received via earphone jack 245.

Figure 3A:
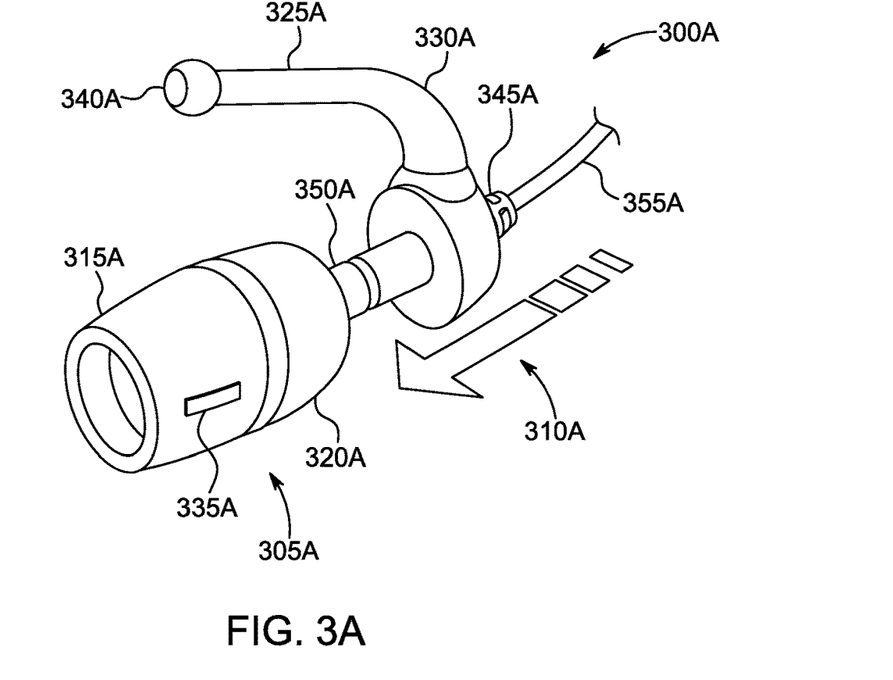
FIGS. 3A and 3B show alternative earphone assemblies that may be used to apply stimulation in combination with audio playback.
Figure 3B:
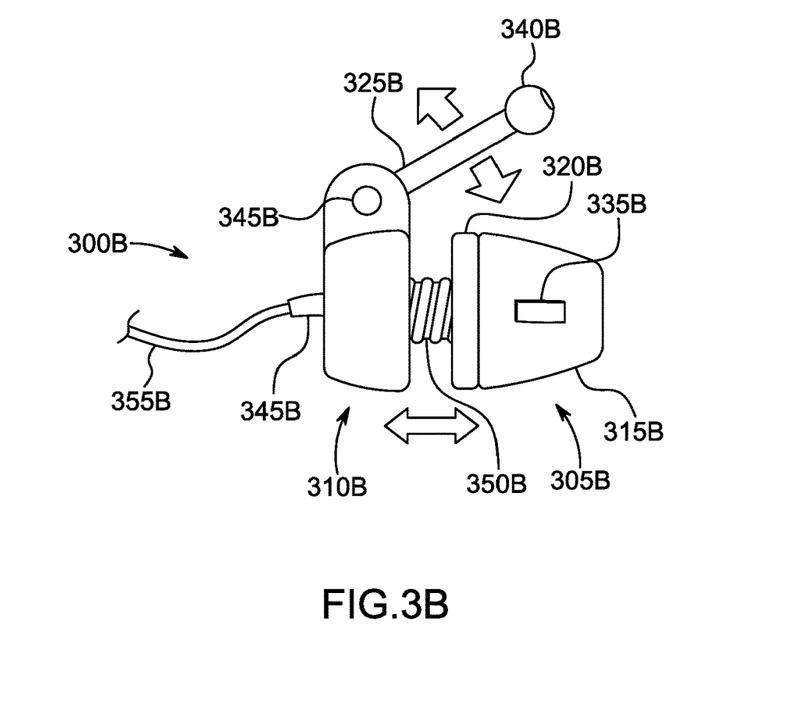

Referring to the alternative earphone assemblies 300A and 300B depicted in FIGS. 3A and 3B, a listening unit 305A, 305B extends from a probe unit 310A, 310B. The probe arms 325A, 325B extend upwardly from the probe units 310A, 310B, and the probe arms 325A, 325B terminate in (bulbous) electrode contacts 340A, 340B. The probe arm 325A of the earphone assembly 300A includes a bendable elbow 330A for positioning and repositioning the electrode contact 340A so as to make contact with the targeted vagus nerves in the ear. The probe arm 325B of earphone assembly 300B is pivotable via probe joint 345 to allow adjustment of the angle of the probe arm 325B relative to the listening unit 305B. The listening units 305A, 305B include earbuds 315A, 315B extending from rear supports 320A, 320B, respectively. Protruding from earbuds 315A, 315B are electrode contacts 335A, 335B, respectively, which are positioned for applying electrical stimulation via the ear canal when the earbuds 315A, 315B are situated in the ear canal of a user. It is noted that, although the exemplary versions in the figures show each earphone assembly with two contact electrodes, three or more electrode contacts may be incorporated as desired. In versions with three or more electrodes, not all electrode contacts would necessarily be used for electrical stimulation at the same time.

Figure 3C:
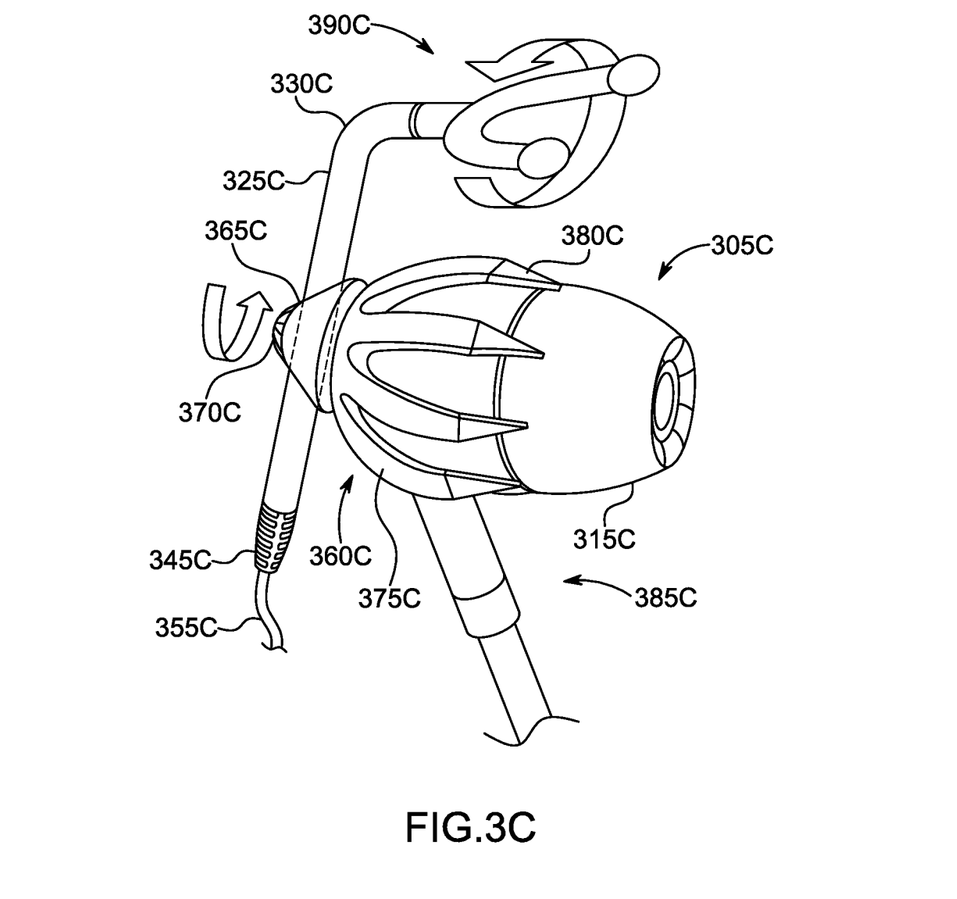
FIG. 3C shows an exemplary clawed grabber with electrodes secured thereto for use with existing (personal) earbuds.

Referring to FIG. 3C, an exemplary claw-like earbud interface 360C allows users to incorporate stimulation functionality with personal earbuds 315C. Interface 360C includes an interface body 365C sandwiched between an interface adjustment knob 370C (or other adjusting mechanism) and a set of gripping "claws" 375C (or other flanges/protrusions). The claws 375C may be flexible, made of (for example) a silicone rubber or another elastomer so as to be able to more easily accommodate (grab) objects having a variety of shapes. The claws 375C may alternatively be rigid, in which case they would preferably have a portion with a shape that is complementary to a portion of the earbud 315C to be grabbed. The adjustment knob 370C, located at a posterior end of the interface 360C, allows for adjustment of the grip (i.e., grabbing strength). Specifically, turning the know allows the user to change how loosely or tightly the claws 375C hold on to an object. Various mechanisms may be used to provide such adjustability. For example, turning the knob 370C may "pull" the claws 375C closer towards the knob 370C via screw-like interaction, effectively "shortening" the claws 375C (i.e., decreasing the extent to which they protrude from the body 365C). As the claws 375C are retracted into the tapered body 365C, the claws 375C are brought closer together, allowing the interface 360C to "bite" or "grip" the earbud 315C. The claws 375C may have tapered ends 380C (or ends with other desired shapes) to allow them flexibility in gripping objects of various shapes and configurations.

The body 365C of the claw-like interface 360C includes an opening for receiving and securing electrodes. In FIG. 3C, a probe arm 325C includes a bendable elbow 330C, and terminates in a pair of electrode prongs 390C. The electrical stimulation signal can be received via cord 355C, which is secured to probe arm 325C via a stimulator jack 345C. The probe arm can be adjustable by sliding ("up" and "down") with respect to the interface body 365C, and by rotating about a long axis of the probe arm 325C. The opening of the interface 360C may be sized to friction fit (i.e., fit "snug") with probe arm 325C so that as it can maintain its position relative to the interface body 365C after adjustment. Advantageously, the interface 360C allows users to conveniently attach to preferred electrodes and earbuds, bringing together sound and stimulation functionality provided by independent devices. In certain embodiments, a user may only need electrodes (without an amplification device). If a user has electrodes to connect to a separate stimulation device (such as a TENS device), they can connect the cord 355C to the electrode input of their preferred stimulation device. The input of the sound/signal can be attached to preferred audio devices via earbud cord 385C.

The listening units 305A, 305B are adjustably separable from the probe units 310A, 310B, respectively, such that a distance/gap between them is adjustable. In the earphone assembly 300A shown in FIG. 3A, one or both of the listening unit 305A and the probe unit 310A can slide relative to a shaft 350A to bring the earphone and probe units 305A, 310A, respectively, closer together or to pull them farther apart to accommodate different users and applications. In the earphone assembly 300B shown in FIG. 3B, one or both of the listening unit 305B and the probe unit 310B complementarily screw relative to a shaft 350B to bring the earphone and probe units 305B, 310B, respectively, closer together or to pull them farther apart to accommodate different users and applications. It is noted that the adjustability of the earphone assemblies illustrated in the figures, and in particular, the ability to adjust the position of the electrode contacts, allows the electrode contacts to reach most parts of the ear. This allows the electrodes to be used to stimulate areas of the ear that are without a vagus nerve distribution, but that may nonetheless be associated with therapeutic/preventative functions (such as, for example, auricular acupuncture points). Moreover, using wired extensions interfacing with auxiliary amplified electrical signal output ports (discussed above), the system can be used to apply electrical stimulation to other parts of the body as well.

The sound signal and amplified electrical signal (as well as power from a power supply) for earphone assemblies 300A, 300B are received via headphone jacks 345A, 345B, respectively. Cords 355A, 355B entering the headphone jacks 345A, 345B can pass through the shafts 350A, 350B and be secured to the rear supports 320A, 320B, respectively, to help secure the listening units 305A, 305B to the probe units 310A, 310B.

Referring to the headphone configuration of exemplary earphone assemblies in FIGS. 4A-4D, a headphone 400 includes a body 405 from which left and right listening portions ("earpads") 405, 410 (which are placed over the left and right ears, respectively) extend. Secured to each earpad 405, 410 is an electrode assembly. Extending from the inner side of each earpad 405, 410 (i.e., the side facing the ear when headphone 400 is worn by a user) are electrodes 450. Extending from the outer side of each earpad 405, 410 (i.e., the side opposing the inner side) are electrode grips 460 as exemplary adjustment mechanisms.

The electrodes 450 and electrode grips 460 are connected by shafts 470. The shafts 470 is preferably flexible so that it can be rotated/twisted, bent (between, for example, zero and 180 degrees), or otherwise manipulated to position the electrodes 450 on the skin of the ear or its surroundings, as desired. The effective "length" or distance that electrodes 450 protrude from earpads 405, 410 can also be adjusted by pushing/pulling on the grip 460. When stimulation is not to be applied, the electrodes 450 can be bent, pulled, twisted, or otherwise adjusted so they do not contact with the skin (see FIG. 4A). When the electrodes 450 are to be used, they can be erected so that they touch the ear for applying stimulation (see FIG. 4B)

Figure 4A:
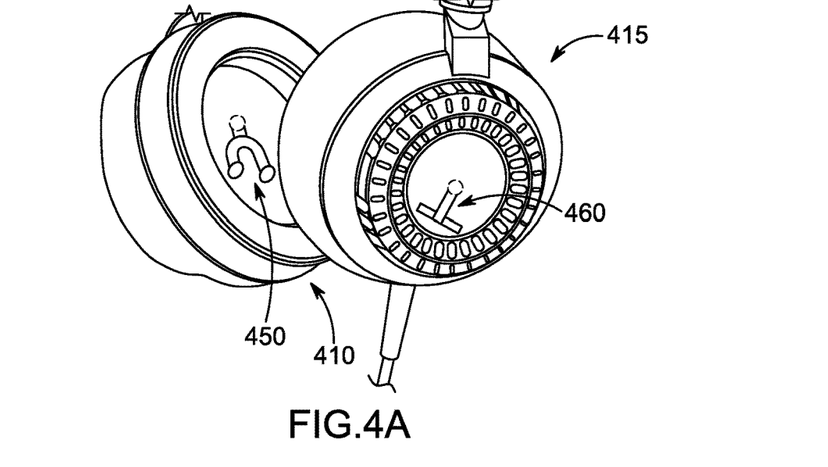
FIGS. 4A-4D show alternative earphone assemblies having exemplary headphone configurations that may be used to apply stimulation in combination with audio playback, with an optional cover/concealer for protecting the privacy of users. Such headphone configurations may be preferred for some populations (such as children or others) when contact with the ear canal (because of, for example, ear canal sensitivity) is not desired, and/or when the noise-reduction provided by ear pads is desired.
Figure 4B:
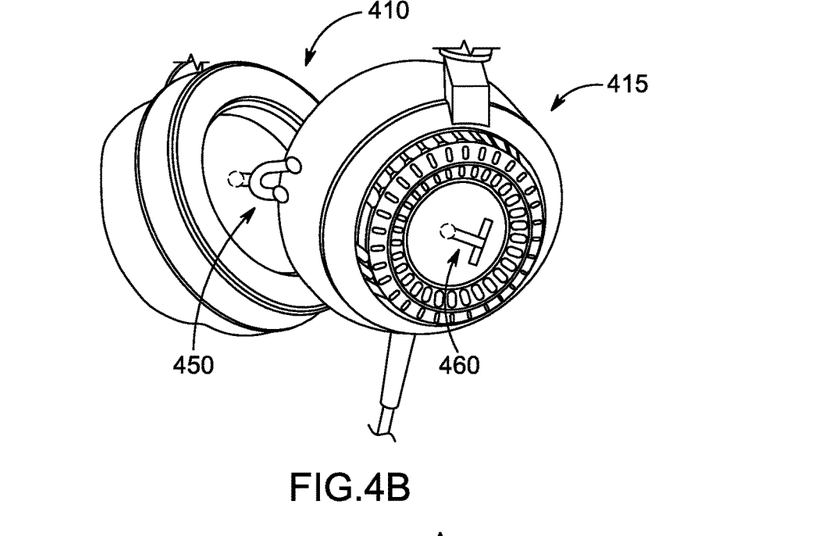
Figure 4C:
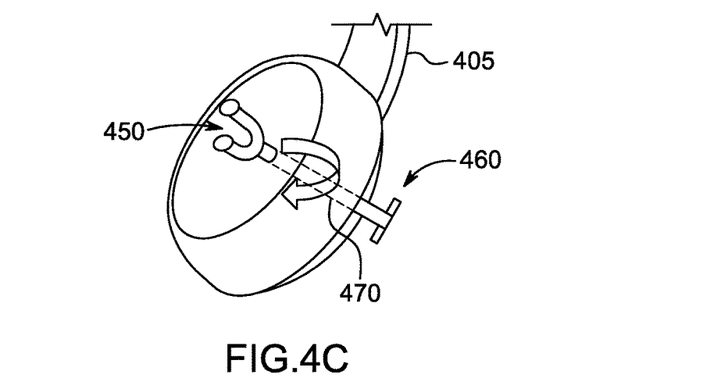
Figure 4D:
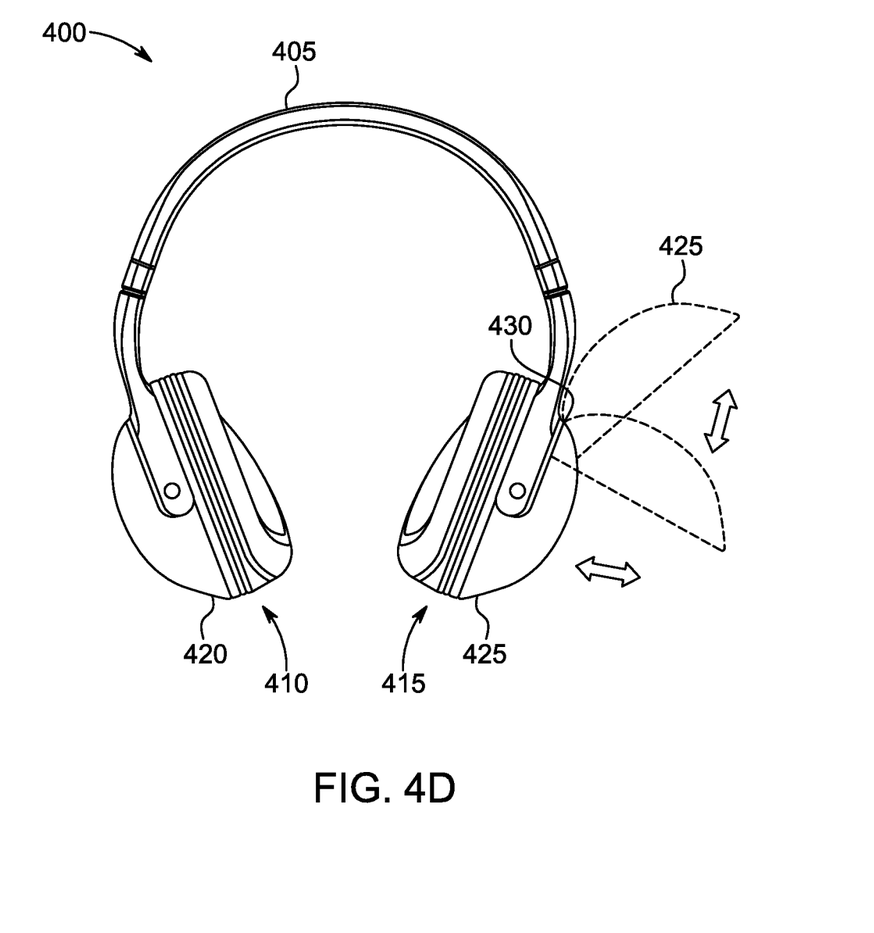

To maintain privacy, a privacy cover/concealer 425 may be used to cover the outer sides of the earpads 405, 410 so as to conceal the grips 460 of the electrode assemblies. By not leaving the electrode assembly exposed, a user may feel more comfortable using headphones that deliver electrical stimulation in public or otherwise when they are not alone. The privacy cover/concealers 425 may be pivotably secured to the earpads 405, 410 via cover hinges 430, allowing a user to remove the cover 425 when adjusting the electrodes 450 via grip 460, and to replace the cover 425 after adjustments have been made. When the covers 425 are concealing the grips 460, the headphone 400 appears to be a "regular" headphone that emits sound without the ability to provide electrical stimulation.

Figure 5:
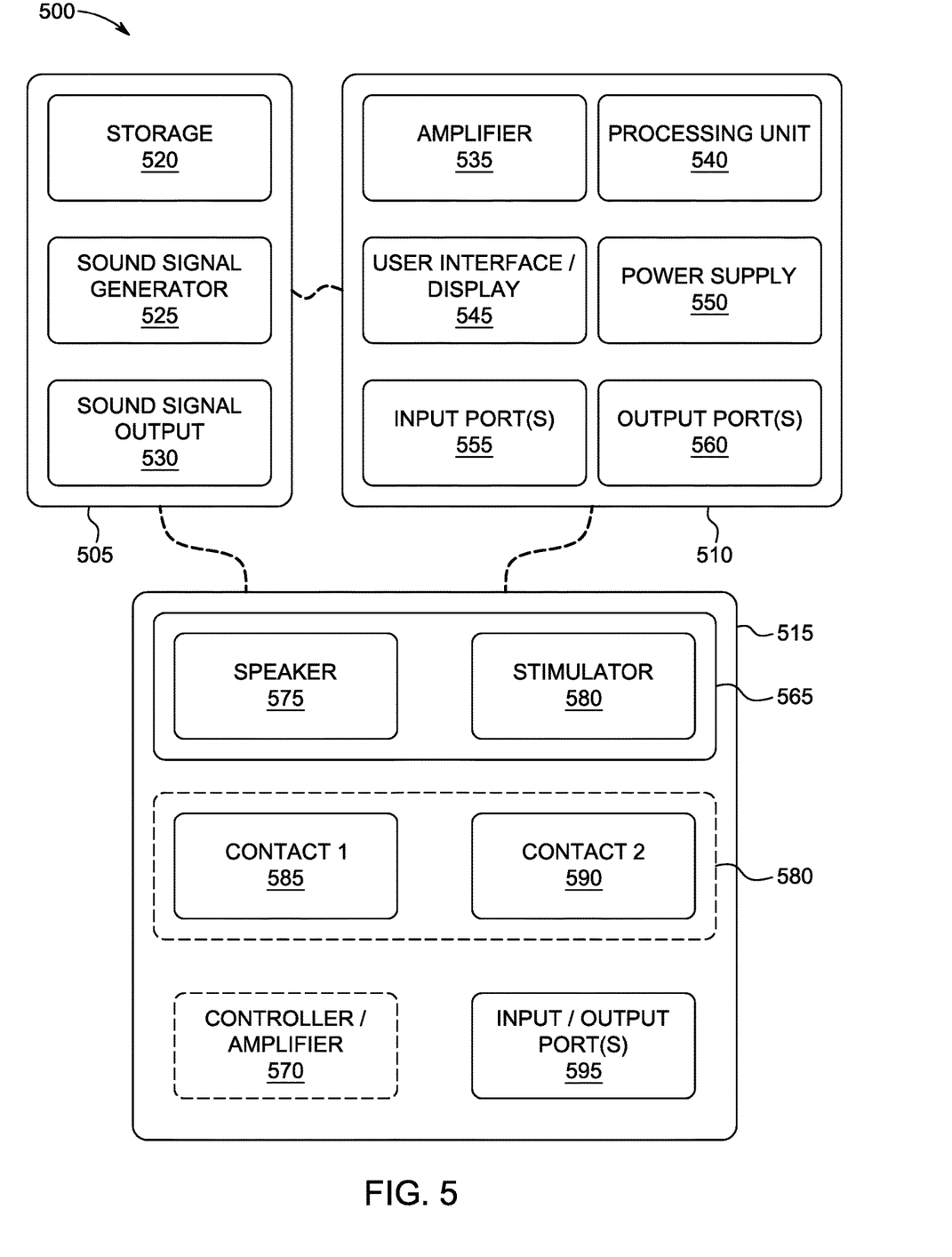
FIG. 5 is an exemplary transcutaneous vagus nerve stimulation (tVNS) system, with a sound source, a control module, and an earphone assembly in various potential configurations.

Referring to the exemplary tVNS system 500 in FIG. 5, a sound source 505 includes a storage medium/memory 520, a sound signal generator 525, and a sound signal output 530 (such as a port for a headphone jack). The sound source 505 could be any suitable device able to output a sound signal, including a smartphone, tablet, computer, radio, media player (i.e., a music player such as an iPod, a video player, and so on), etc. The media files, which could be digital sound files containing (for example) music or audiobooks, or digital video files (such as television shows or movies), are stored in storage 520 and accessed by the sound signal generator 525 when the files are to be "played." The sound signal would be accessed via the sound signal output 530.

The control module 510 includes an amplifier 535 for amplifying the sound signal to generate an amplified electrical signal. The control module 510/amplifier 535 can be connected to the sound source 505 wirelessly or using wires. The sound signals (music or other audio) from many sound sources would be expected to have a magnitude around 10 mV, which may be amplified to generate an electrical signal with a magnitude of, for example, 80V. The amplifier may be controlled to function continuously or intermittently, such as 50 millisecond amplification intervals followed by 950 milliseconds without amplification. The amplifier may also be controlled to produce a regular electrical pulse with adjustable frequencies independent of the sound input, similar to TENS systems.

The control module 510 includes a processing unit 540, which may have a processor, one or more memory modules, and instructions in the form of software (which can be loaded into the memory), firmware, hardware, or any combination thereof. The components of the processing unit 540 are involved in coordination and implementation of the functionality of the system 500 (i.e., control functions) by interfacing with the other components of system 500. A user interface/display 545 allows users to enter commands (that can be executed via the processing unit 540) related to, for example, treatment parameters (duration, frequency, magnitude, etc.), and to receive information regarding, for example, status, progress, etc. The power supply 550, which may be, for example, a rechargeable battery or portable charger, delivers the electrical energy used by the amplifier and other components. The input ports 555 are used to receive, for example, the sound signal that is to be amplified, and the output ports 560 can be used to provide, for example, the amplified electrical signals used by the earphone assembly 515 to apply stimulation.

The earphone assembly 515 includes a listening unit 565, a stimulator/stimulating unit 580, and intput/output ports 595. The listening unit 565 includes a speaker 575 (i.e., a loudspeaker or electroacoustic transducer) for emitting the sounds to be played through the earphone assembly 515. The stimulator 580 includes stimulating electrode contacts 585, 590, and may be part of the listening unit 565 (as with electrode contacts that protrude from earbuds) or separate therefrom (such as with electrode contacts that are part of a probe unit), as suggested by the dotted lines. The earphone assembly 515 may also include a controller/amplifier 570 (or any/all of the components of the control module 510) as deemed suitable. The intput/output ports 595 allow the earphone assembly to interface with other components of the system 500 to send/receive signals therefrom.

It is noted that the sound source 505, the control module 510, and the earphone assembly 515 and their components can be rearranged and reconfigured as desired (some examples of which are suggested by the dotted lines in FIG. 5). For example, the sound source 505 and the control module 510 can be combined with each other, and the combination interfaced with the earphone assembly 515. Similarly, the control module 510 and the earphone assembly 415 can be combined, and that combined device connected with a sound source 505. Alternatively, the sound source 505, control module 510, and earphone assembly 515 can be combined into one integrated device that does not require a separate sound source 505 to function.

Figure 6:
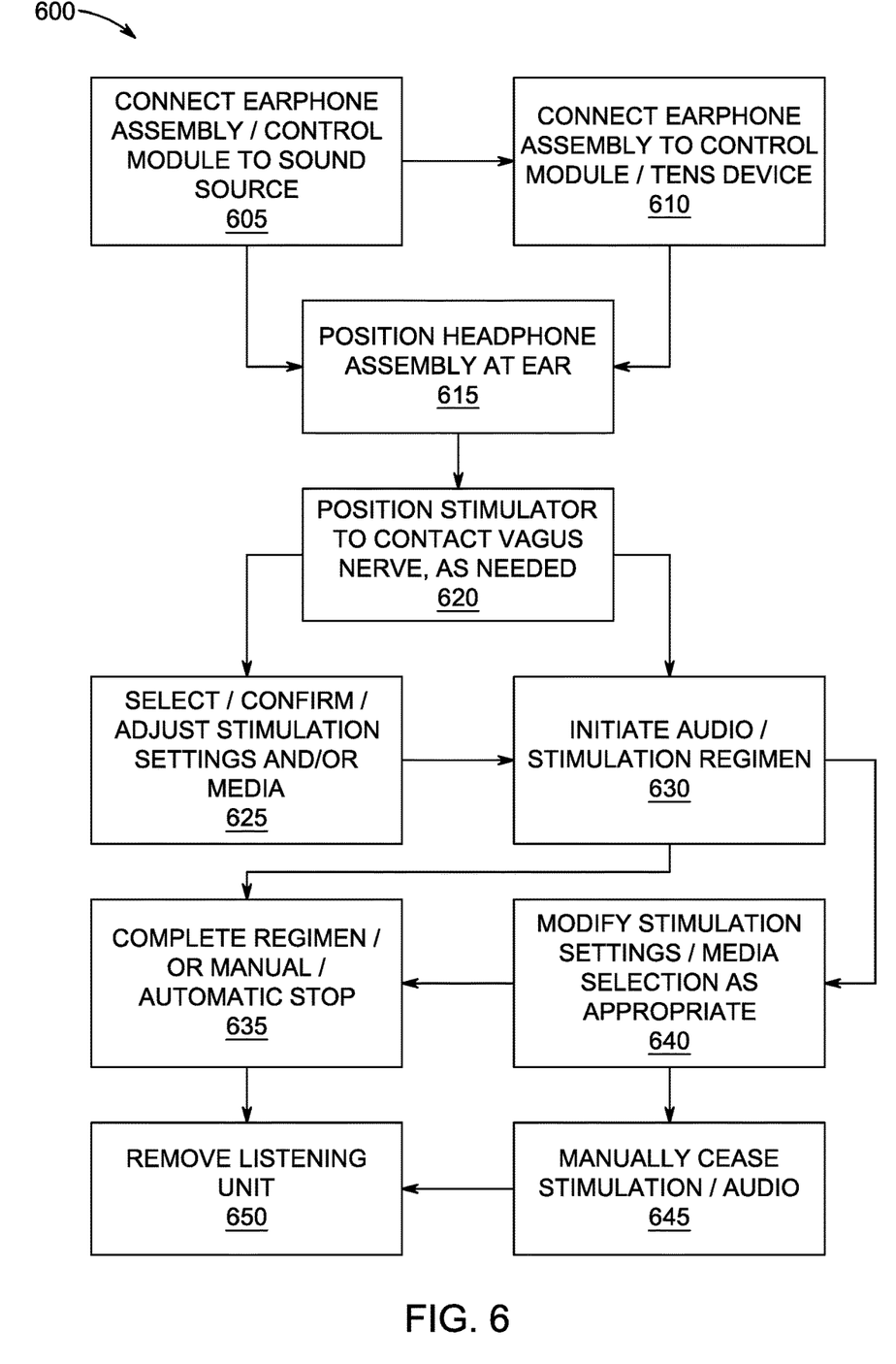
FIG. 6 provides a flowchart with a set of steps involved in implementing exemplary methods for tVNS.

Referring to flowchart 600 in FIG. 6, a user may begin by connecting the control module (or, if the functions of the control module are incorporated in the earphone assembly, connecting the earphone assembly) to the sound source (605). If the control module and the earphone assembly are separate components, such that in step (605) the control module was connected to the sound source, the user next connects the earphone assembly to the control module and/or to another stimulation device or electrical signal generator, such as a TENS device (610). Users may wish to use their own stimulation devices (such as TENS devices) because such devices may provide particular stimulation regimens, such as desired stimulation frequency, pattern, and waveform options. Either way, the user may next place the earphone assembly at his/her ear (615). If the earphone assembly includes a listening unit/earbud, this step may involve placing the listening unit such that the earbud is at least partially inserted in the ear canal. By sizing the earbud to have a slightly larger diameter than that of the ear canal, insertion in the ear canal provides an interference fit ("press fit" or "friction fit") that serves to removably secure the earphone assembly to the user's ear (such that earphone assembly need not, for example, be held in place using one's hand). In embodiments in which the earphone assembly does not include an earbud to be inserted in the ear canal, the earphone assembly could be secured to the ear by, for example, placing a resiliently flexible bridge connecting two earpieces over the user's head.

The stimulator is next positioned such that the electrode contacts to be used can access/reach the vagus nerve (or other region to be stimulated) (620). If the ear canal is to be stimulated using electrode contacts protruding from the earbud, step (620) may not be needed once the earbud has been positioned in the ear canal in step (615); otherwise, step (620) may involve (for example) pivoting or otherwise adjusting a probe arm to position the stimulator. The user may optionally select and/or confirm the settings to be used to apply stimulation, or adjust preset stimulation parameters (625); here, the user may also select what media is to be played if not already selected. Once the settings have been selected, the user may initiate the audio and/or the stimulation regimen to be used (630). While the stimulation regimen is progressing, the user may modify the stimulation settings and/or the media being played (540), and/or perform a manual stop of the stimulation and/or the audio (635, 645). Alternatively, the stimulation may be allowed to continue until it is complete, or until there is otherwise an automated stop (resulting from, for example, detection of a fault, such as a short circuit of electrodes) (635). The user may then remove the earbud from his/her ear (650) and disconnect the sound source if desired.

The present invention has been described in terms of one or more preferred embodiments, and it should be appreciated that many equivalents, alternatives, variations, additions, and modifications, aside from those expressly stated, and apart from combining the different features of the foregoing versions in varying ways, can be made and are within the scope of the invention. It should be appreciated that the invention is applicable to other procedures and to achieve other objectives as well. Following are additional examples. These examples are not to be construed as describing the only additions and modifications to the invention. It is expressly contemplated that any of the processes or steps described herein may be combined, eliminated, or reordered. Accordingly, this description is meant to be taken only by way of example, and not to otherwise limit the scope of this invention. The patentable scope of the invention is defined by the claims and may include other examples that occur to those skilled in the art.

For example, as discussed above, it is noted that the term "earphone" is not intended to limit the configuration of the system to a headphone-like or earbud-like designs. Additionally, although the electrical signal used to apply stimulation is discussed above as being generated by amplifying the sound signal, the electrical signal could alternatively or additionally be generated by a signal generator. Further, although in above discussion the signals are generally transmitted using wires, the system could be configured to transmit and receive, for example, the sound signal wirelessly. Furthermore, it should also be appreciated that different components of the systems and methods discussed above and depicted in the figures can be implemented using hardware, software, single integrated devices, multiple devices in wired or wireless communication, or any combination thereof.

What is claimed is:

1. A transcutaneous peripheral nerve stimulation system comprising:
   an amplifier configured to receive a sound signal from a sound source and amplify the sound signal to generate an amplified electrical signal; and
   an earphone assembly including:
      a listening unit including a speaker configured to receive the sound signal and emit audio according to the sound signal;

a stimulator coupled to the amplifier, the stimulator being configured to apply, as audio is emitted from the speaker, the amplified electrical signal from the amplifier to transcutaneously electrically stimulate a peripheral nerve of a subject; and a probe arm extending from the listening unit, the probe arm branching into first and second prongs at a distal end thereof, wherein first and second electrode contacts extend from the first and second prongs, respectively, of the probe arm;

wherein the probe arm is coupled to the listening unit via a first rotary joint, the probe arm being rotatable about a first axis defined by the probe arm; and wherein the first and second prongs are coupled to the probe arm at a second rotary joint such that the first and second prongs together rotate about a second axis.

2. The system of claim 1 wherein the earphone assembly includes a headphone having left and right listening portions, each listening portion having at least one electrode situated at an inner side, and an adjusting mechanism situated at an outer side opposing the inner side, each adjusting mechanism being configured to adjust an angle of the respective electrode.

3. The system of claim 2 further including left and right privacy covers placed over the adjusting mechanisms of the left and right listening portion, respectively, so as to conceal the adjusting mechanism.

4. The system of claim 1 wherein the earphone assembly is configured to receive the sound signal directly from the sound source that provides the sound signal that is amplified by the amplifier.

5. The system of claim 1 wherein:
the earphone assembly further includes a listening unit sized to be at least partially received in an ear canal of a subject;
the stimulator protrudes from the listening unit; and
the earphone assembly is configured such that when the listening unit is in an ear canal of a subject, the stimulator is positionable to reach and electrically stimulate a vagus or other nerve of a subject.

6. The system of claim 1 wherein the stimulator includes at least first and second electrode contacts extending radially outwardly from the earphone assembly.

7. The system of claim 1 wherein:
the earphone assembly further includes a listening unit and a probe arm extending from the listening unit; and
the stimulator includes a first electrode contact protruding from a distal end of the probe arm, and a second electrode contact protruding from the listening unit.

8. The system of claim 1 wherein the stimulator includes at least one electrode contact having a conductive elastomer.

9. The system of claim 1 wherein:
the earphone assembly further includes a listening unit and a probe unit coupled to the listening unit; and
the stimulator is at least partially incorporated in the probe unit; and
a separation between the listening unit and the probe unit is adjustable.

10. The system of claim 9 further including a shaft extending between the listening unit and the probe unit, wherein the separation between the listening unit and the probe unit is adjustable by retractable insertion of the shaft into one or both of the listening and probe units.

11. The system of claim 1 wherein the amplifier is incorporated in the earphone assembly.

12. The system of claim 1 further including a control module configured to control at least one of a frequency and a magnitude of the amplified electrical signal to modulate stimulation applied by the stimulator, wherein the amplifier is incorporated in the control module.

13. The system of claim 1 further including a filter configured to only allow frequencies within a predetermined range to be amplified by the amplifier to generate the amplified electrical signal.

14. The system of claim 1 further including a sound source outputting the sound signal received by the amplifier.

15. A transcutaneous peripheral nerve stimulation method comprising:
receiving a sound signal from a sound source;
amplifying the sound signal using an amplifier to generate an amplified electrical signal;
emitting audio according to the sound signal using a speaker in a listening unit;
as audio is emitted from the listening unit, transcutaneously electrically stimulating a peripheral nerve of a subject by applying the amplified electrical signal using a stimulator coupled to the amplifier;
wherein the listening unit includes a probe arm extending therefrom, the probe arm branching into first and second prongs at a distal end thereof, wherein first and second electrode contacts extend from the first and second prongs, respectively, of the probe arm;
wherein the probe arm is coupled to the listening unit via a first rotary joint, the probe arm being rotatable about a first axis defined by the probe arm, and wherein the first and second prongs are coupled to the probe arm at a second rotary joint such that the first and second prongs together rotate about a second axis.

16. A transcutaneous peripheral nerve stimulation system comprising:
a sound signal input port configured to receive a sound signal from a sound source;
an amplifier configured to amplify the sound signal received via the sound signal input port to generate an amplified electrical signal;
a listening unit having a speaker for emitting audio, and a stimulator coupled to the listening unit; and
a controller configured to:
emit audio through the speaker according to the sound signal received via the sound signal input port; and
simultaneously apply the amplified electrical signal to the stimulator so as to transcutaneously electrically stimulate a peripheral nerve of a subject; and
wherein the listening unit includes a probe arm extending therefrom, the probe arm branching into first and second prongs at a distal end thereof, wherein first and second electrode contacts extend from the first and second prongs, respectively, of the probe arm;
wherein the probe arm is coupled to the listening unit via a first rotary joint, the probe arm being rotatable about a first axis defined by the probe arm, and wherein the first and second prongs are coupled to the probe arm at a second rotary joint such that the first and second prongs together rotate about a second axis.

17. The system of claim 16 wherein the first and second prongs separated by a gap.

* * * * *